(12) United States Patent
Göbel

(10) Patent No.: US 10,952,737 B2
(45) Date of Patent: Mar. 23, 2021

(54) TAMPONADE FOR NASAL CAVITIES OR SINUS CAVITIES

(71) Applicant: Creative Balloons GmbH, Waghäusel (DE)

(72) Inventor: Fred Göbel, Wilhelmsfeld (DE)

(73) Assignee: Creative Balloons GmbH, Waghausel (DE)

( * ) Notice: Subject to any disclaimer, the term of this patent is extended or adjusted under 35 U.S.C. 154(b) by 273 days.

(21) Appl. No.: 15/572,379

(22) PCT Filed: May 9, 2016

(86) PCT No.: PCT/IB2016/000610
§ 371 (c)(1),
(2) Date: Nov. 7, 2017

(87) PCT Pub. No.: WO2016/178080
PCT Pub. Date: Nov. 10, 2016

(65) Prior Publication Data
US 2018/0146967 A1    May 31, 2018

(30) Foreign Application Priority Data

May 7, 2015   (DE) ...................... 10 2015 005 725.1
Nov. 2, 2015  (DE) ...................... 10 2015 014 153.8

(51) Int. Cl.
*A61B 17/12*    (2006.01)
*A61B 17/24*    (2006.01)
*A61M 25/10*    (2013.01)

(52) U.S. Cl.
CPC .... *A61B 17/12104* (2013.01); *A61B 17/1204* (2013.01); *A61B 17/12136* (2013.01);
(Continued)

(58) Field of Classification Search
CPC .......... A61B 17/1204; A61B 17/12136; A61B 17/24; A61B 17/12163; A61B 17/1688;
(Continued)

(56) References Cited

U.S. PATENT DOCUMENTS 6,607,546 B1    8/2003   Murken
2004/0243172 A1*  12/2004  Hogle .................... A61B 17/24
                                                        606/199
(Continued)

FOREIGN PATENT DOCUMENTS

DE    3712502 A1    10/1988
DE    4010975 A1    10/1991
(Continued)

OTHER PUBLICATIONS

English machine translation of DE 20320631U1 (Year: 2005).*

*Primary Examiner* — Katrina M Stransky
(74) *Attorney, Agent, or Firm* — Pandiscio & Pandiscio

(57) ABSTRACT

A tamponade for nasal cavities or sinus cavities for tamponading a cavity of the nasal tract in the region of an ostium leading to the cavity with uniform force, comprising a thin-walled balloon which is made from a soft foil-like, only slightly expandable, smoothly folding polyurethane material, with a wall thickness in the range of 5 to 50 µm, which is already completely shaped with the required tamponade dimensions or greater at the time of production, and can therefore be expanded without application of filling pressure, and said balloon occupies the respective, generally irregular-shaped cavity and the ostium of same when in the filled condition, through the development of forces that are as uniform as possible on the structures exposed to the balloon in such a way that a distal segment of the balloon is located inside the cavity where a tamponade is to be applied, a proximal segment of the balloon is located upstream of the cavity and a transostial segment of the balloon extends
(Continued)

Figure 1:
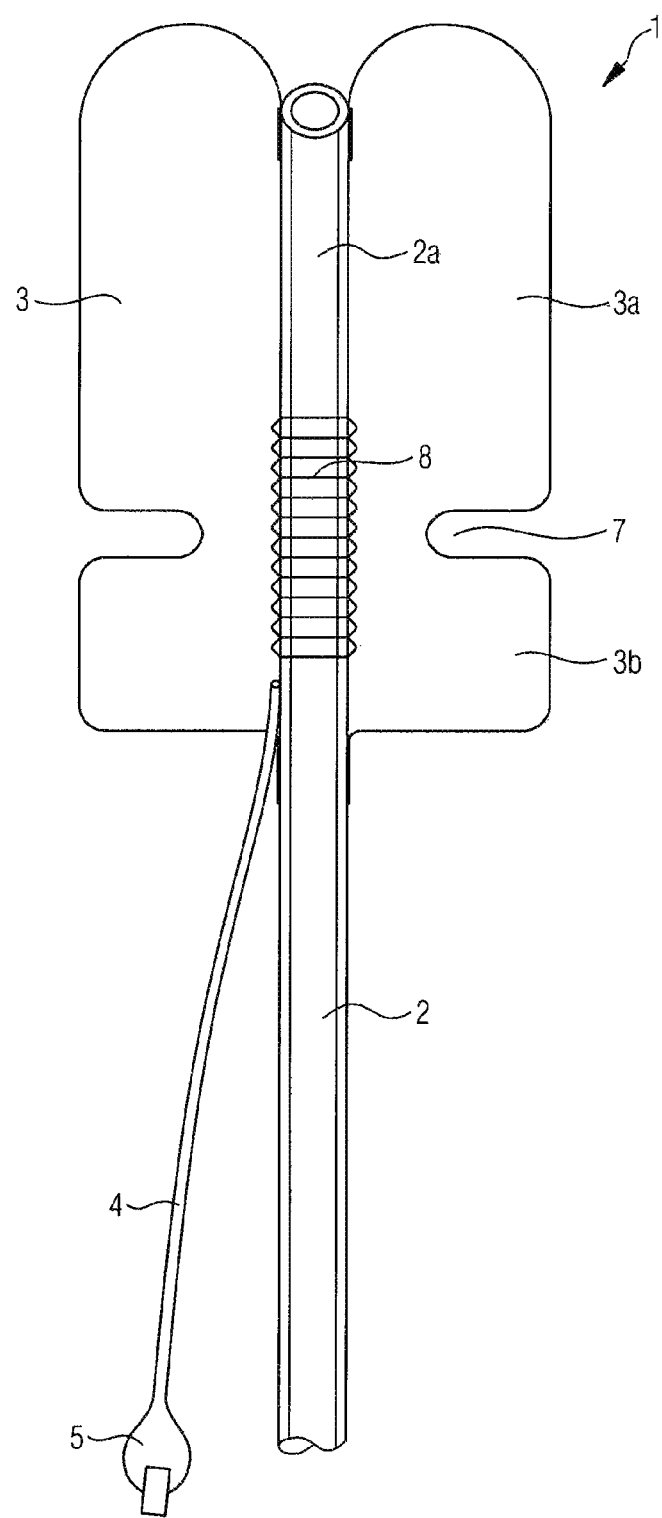

through the ostium and connects the distal segment of the balloon to the proximal segment of the balloon, wherein the transostial segment of the balloon is tapered relative to the proximal and distal segments of the balloon in the deployed state of the balloon, and the nasal cavity or sinus cavity tamponade is anchored in the transition region and reliably secured in position.

22 Claims, 8 Drawing Sheets

(52) U.S. Cl.
CPC ........ *A61B 17/12163* (2013.01); *A61B 17/24* (2013.01); *A61M 25/1006* (2013.01); *A61M 25/1011* (2013.01)

(58) Field of Classification Search
CPC .............. A61B 1/233; A61M 25/1006; A61M 25/1011; A61M 2210/0681; A61M 31/00
See application file for complete search history.

(56) References Cited

U.S. PATENT DOCUMENTS

| | | | |
|---|---|---|---|
| 2005/0245906 A1* | 11/2005 | Makower | ............... A61B 5/411 |
| | | | 604/891.1 |
| 2015/0065810 A1* | 3/2015 | Edgren | .................. A61B 17/24 |
| | | | 600/249 |

FOREIGN PATENT DOCUMENTS

| | | |
|---|---|---|
| DE | 20320631 U1 | 12/2004 |
| GB | 2258811 A | 2/1993 |

\* cited by examiner

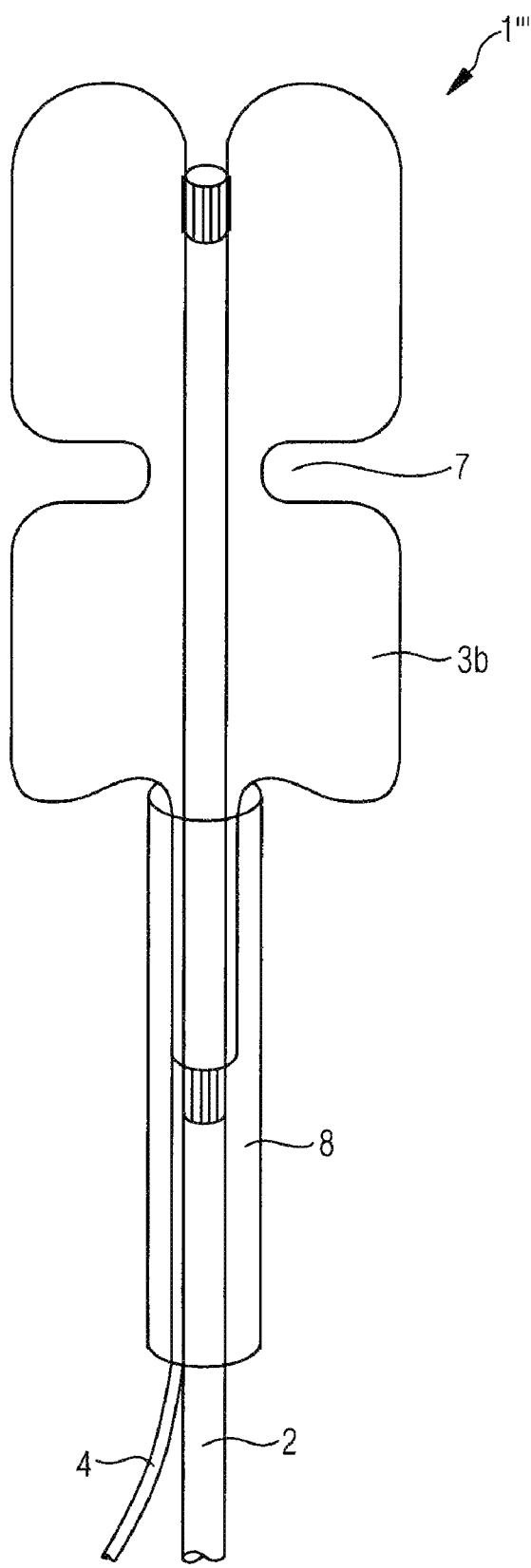

TAMPONADE FOR NASAL CAVITIES OR SINUS CAVITIES

REFERENCE TO PENDING PRIOR PATENT APPLICATIONS

This patent application claims benefit of International (PCT) Patent Application No. PCT/IB2016/000610, filed 9 May 2016 by Creative Balloons GmbH for TAMPONADE FOR NASAL CAVITIES OR SINUS CAVITIES, which claims benefit of: (i) German Patent Application No. DE 10 2015 005 725.1, filed 7 May 2015 and (ii) German Patent Application No. DE 10 2015 014 153.8, filed 2 Nov. 2015, which patent applications are hereby incorporated herein by reference.

FIELD OF THE INVENTION

The present invention is directed to a tamponade for nasal cavities or sinus cavities for tamponading a cavity of the nasal tract in a uniform force-applying way in the region of are ostium leading to the cavity.

BACKGROUND OF THE INVENTION

During the surgical treatment or surgical opening of partially or completely closed access openings (ostia) into the sinus cavities (paranasal sinus), it is common for the enlarged ostium to reclose during the subsequent wound healing process. The stenosis of the ostium that develops post-operatively from the formation of granulation and scar tissue can be so pronounced that any benefit from the surgical widening is largely or even entirely lost after just a few weeks.

In order to prevent the recurrence of a stenosis that accompanies wound healing, many surgeons insert tamponading bodies into the surgically enlarged transition from the main nasal cavity to the adjacent sinus cavity. The majority of tamponading elements today consist of fingerstall-like sheaths, into which a small, elastically deformable, sponge-like element is inserted to conform to the surrounding smooth-walled sheath of the fingerstall against the wound area with moderate pressure.

The insertion of a gauze-like strip, with which the ostium itself and the region upstream and downstream of the ostium are filled is likewise established in clinical practice.

The problem with these techniques remains primarily the pain associated with the removal of the tamponading material and the bleeding that often accompanies the removal. With dwell times of up to a week and beyond, the tamponade material can be subject to significant encrustation and anchorage with the wound area, which tear open the wound area with the tamponade is moved and can thereby, in turn, lead to the excessive regeneration or granulation of tissue.

In recent years, tamponade systems based on inflatable balloon bodies have been offered for the post-operative tamponading of the nasal cavity and the sinus cavities. They generally consist of pre-formed balloon components resting on a tube- or pipe-like shaft body. The balloons are usually manufactured of silicone or PVC, are configured with appropriately thick walls and, in the case of silicone, often include the option of a certain elastic expansion of the sheath body when filling pressure is applied. The supporting shaft usually consists of relatively rigid material and permits the surgeon to guide the tamponade. In corresponding balloon tamponades for treating the sinus cavities, the tamponading balloon component narrow in some cases in a waist-like manner in the vicinity of the segment to be placed within the ostium in order to sufficiently secure the balloon body that is to fill the sinus. Additionally, balloon tamponades are known which are equipped with special net-like coverings consisting of cellulose-like materials, which have a localized hemostatic effect.

Problematic in the devices described is primarily the insufficient ability of the balloon to rest flat against the individual shape of the sinus or its respective surface. In particular, the known tamponade techniques do not provide sufficient continuous flat nestling of the balloon sheath material against the wound surfaces in the vicinity of the ostium itself, which are critical to the success of the tamponade.

The way in which the balloon sheath conforms to the respective wound surface is relevant in particular when the prominent structures protruding into the space that is to be tamponaded lead to pressure spikes, which stop the local blood flow and can thereby interrupt and slow the wound healing process. Owing to the inhomogeneous development of forces on the adjacent tissue, as described, conventional balloon tamponades do not allow the surgeon to exercise sufficient control over the various effective tamponade pressures.

A further essential problem with the conventional tamponading of sinus cavity ostia often consists in the complete blockage of free nasal breathing by the patient.

Furthermore, in the majority of tamponades it is not possible to establish adequate ventilation of the tamponaded sinus cavity or the possibility of intermittently rinsing the sinus cavity.

SUMMARY OF THE INVENTION

The present invention offers comprehensive approaches to solving this problem on the basis of balloon sheaths with micro-thin walls that consist of less elastic polyurethane and that have already been formed into residually dimensioned balloon bodies during manufacture, which, once produced, already exceed the measurements of the cavities and ostia or canals they are intended to treat, i.e. they lack the required elastic expansion. Once placed in situ, the residual sheath components fold into the balloon interior, and so prominent structures protruding into the space to be tamponaded are also loosely surrounded in a shell-like manner, and permanent pressure spikes on prominent structures can be largely prevented. If the micro-thin balloon sheath has sufficient residual dimensions, the surface of complexly shaped inner spaces can be almost completely encompassed by the tamponade, and an inhomogeneous application of pressure can be avoided. The tamponading balloon body can thus be configured with generous radial dimensions so as also to encompass the maximum cavity variants with the advantage described.

According to the invention, the length of the tamponade body or its segments can be adapted different ways during positioning.

In an alternative embodiment to the residual diameter, the balloon segment that is placed within the sinus cavity can have a diameter that is smaller than the cavity and can instead be configured with residual length. During placement, the surgeon pushes it into the cavity similarly to a tamponade strip. During filling, the overly long segment compresses and folds in a space-filling manner like an inflatable gauze. Surplus balloon components fold up, and the surface of the cavity is subjected to a largely homogeneous force as a result of the bundle that is formed, thereby largely avoiding local pressure spikes.

The elongation of the balloon segment, which occurs during the filling of the main nasal cavity, can be adjusted by a sleeve element that can be displaced axially on the shaft tube and is limited by the unfolding of the balloon.

To secure the positioning of the tamponade in the ostium, the preferred embodiment of the device is provided with a circular tapering or "waistline" that approximately corresponds to the ostium diameter but preferably exceeds it, so that any excess sheath material also folds radially inward here, and a homogenous application of pressure to the wound surfaces is ensured.

The principle of the shell-like, tension-free folding of excess sheath wall according to the invention makes it possible to generate homogeneous tamponade forces that, using e.g. a balloon pressure gauge when the tamponade is applied and especially during the during the tamponading process, can be adjusted such that they lie below the perfusion pressures required for mucous membrane perfusion and thus below the perfusion pressures required for healing. In this preferred embodiment of the tamponade segments, the barometrically measured filling pressure corresponds approximately to the transmural forces acting upon the mucous membranes and wound surfaces.

Owing to the good anchoring properties of the tamponade in the ostium provided by the possibility of limiting the spatial elongation of the tamponade into the main nasal cavity, it is possible to forgo "stuffing" the main cavity to secure the tamponade body in its position. The main cavity can thus remain open, thereby ensuring unobstructed nasal breathing. Once installed and filled by the surgeon, the shaft element supporting the tamponade balloon can be trimmed to the level of the outer nostril. Accordingly, once the effective tamponading force has been adjusted, the fill line can be sealed e.g. by a clip and likewise cut to the height of the nostril. The tamponade can thus be worn by the patient for longer periods without interfering with nasal breathing or appearance. The quality of the film surface in particular has proven decisive to the quality of the healing of the wound. The flatter the film is, the more uniformly the regenerating tissues that lie against said film can develop. Polyurethane (PUR) balloon bodies that are blow-molded from pre-extruded tubing material while being stretched axially and radially exhibit unsurpassed surface quality. Even when magnified 10,000 times, the PUR surfaces formed in this way still appear completely flat.

Another decisive factor in the healing process is that the sinus cavities are constantly ventilated and that the sinus can also be rinsed through the lumen of the tamponade shaft.

BRIEF DESCRIPTION OF THE PREFERRED EMBODIMENTS

Figure 2:
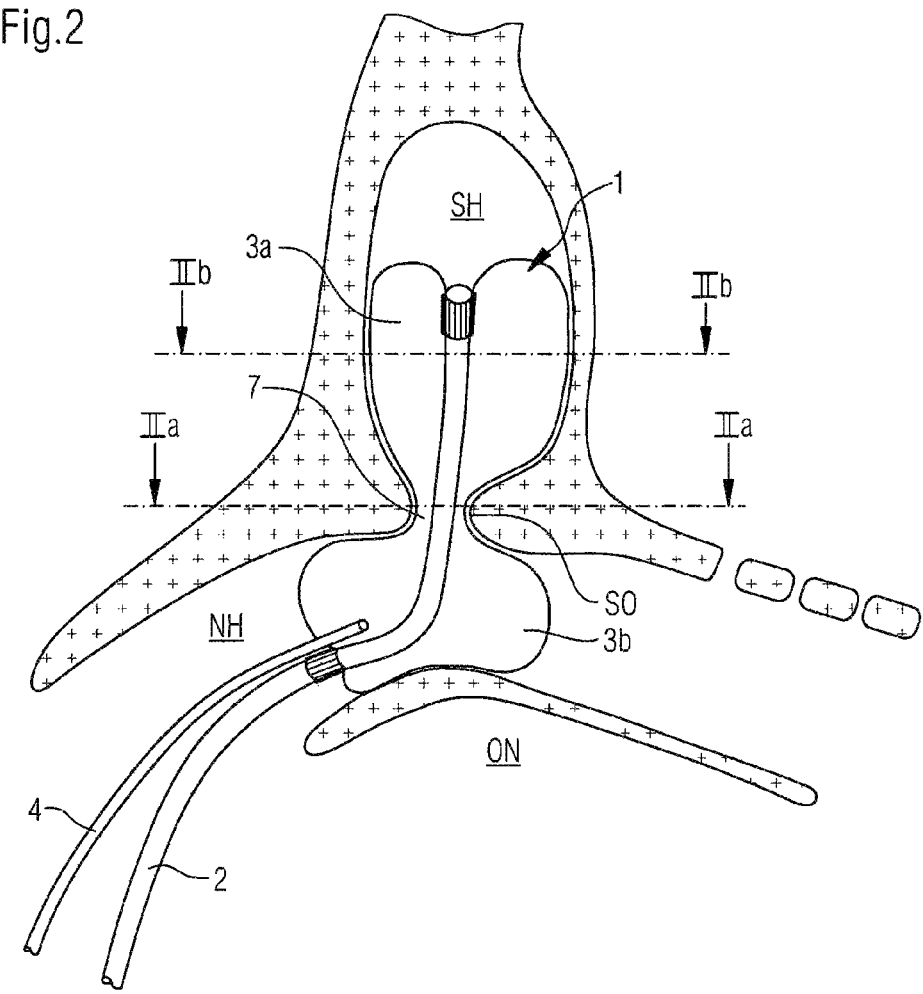
Figure 2A:
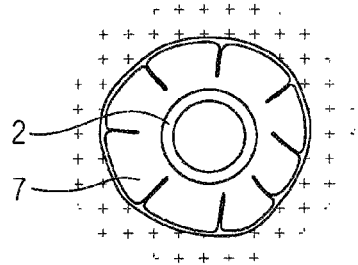
Figure 2B:
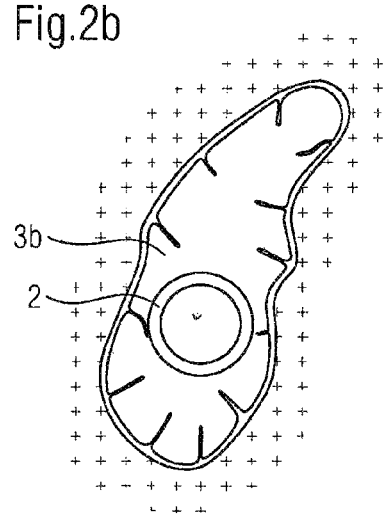
Figure 3:
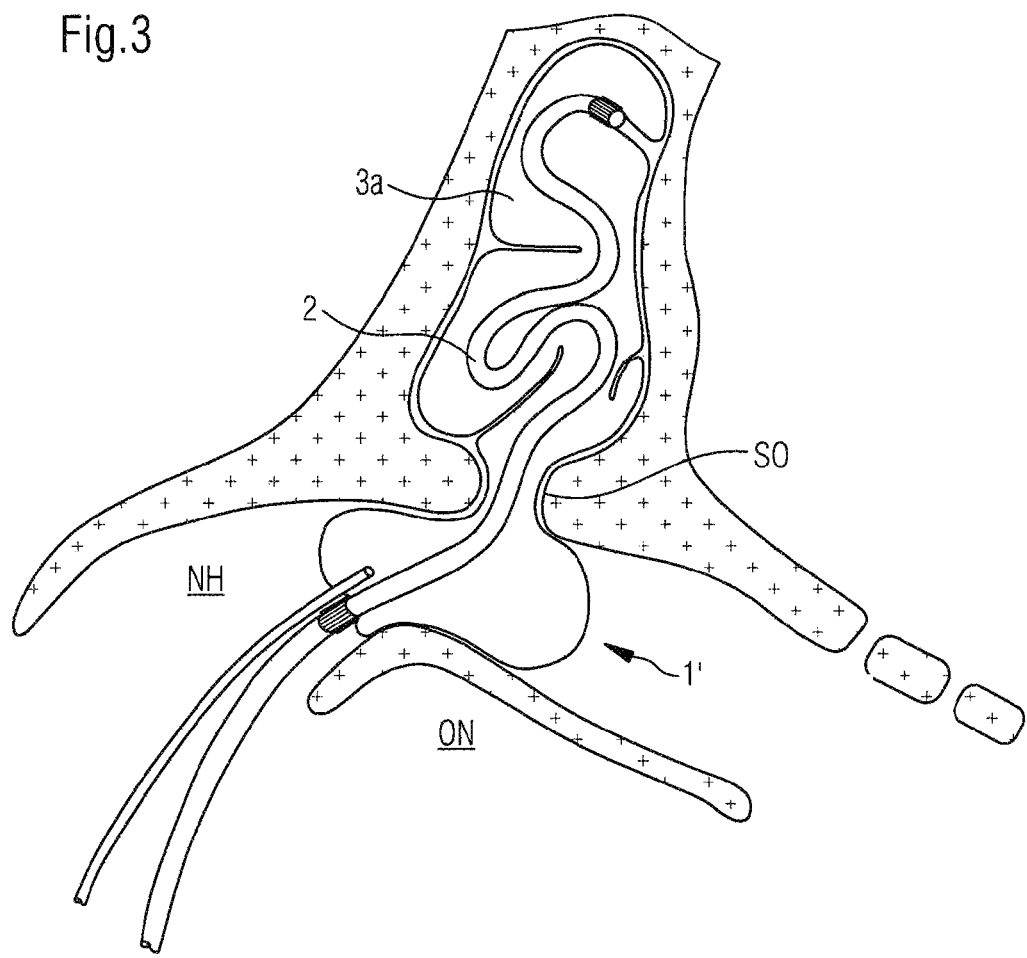
Figure 4:
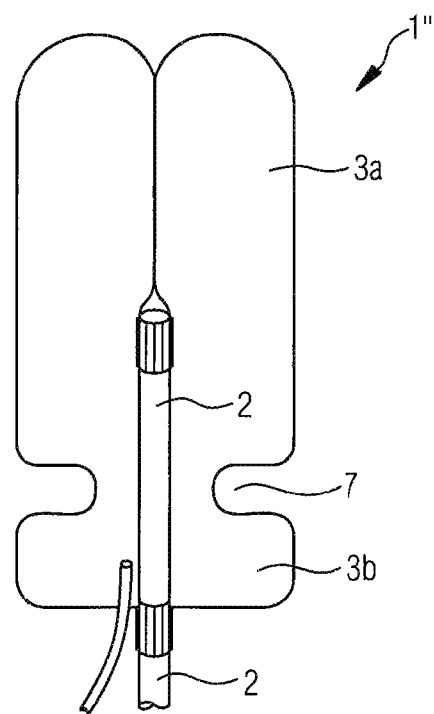
Figure 5A:
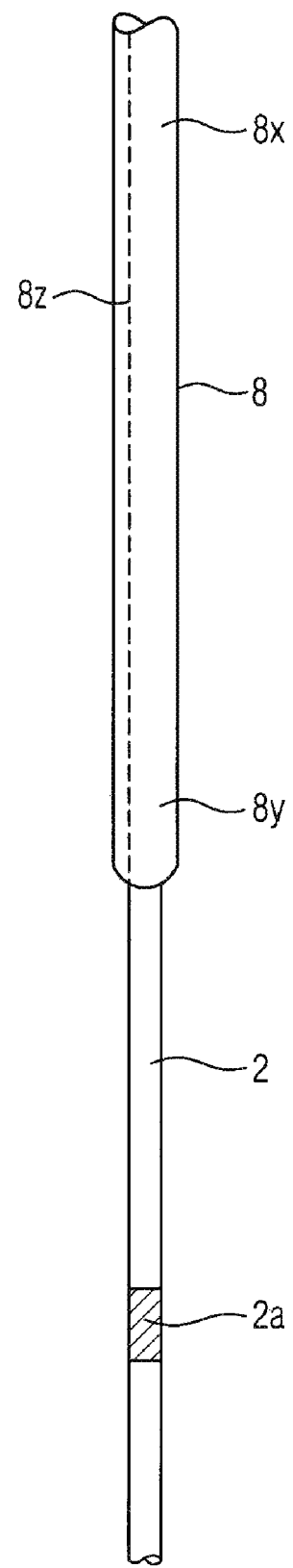
Figure 6:
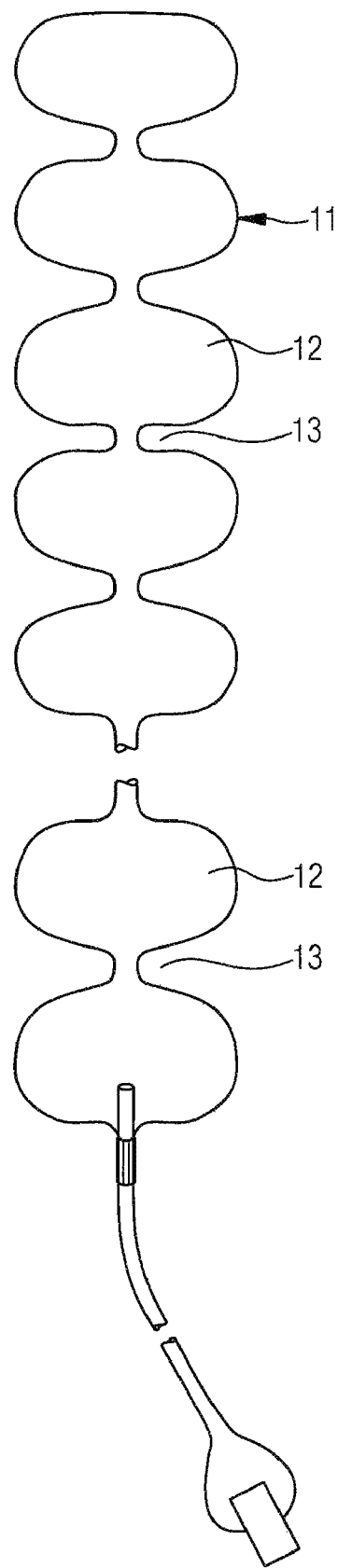
Figure 7:
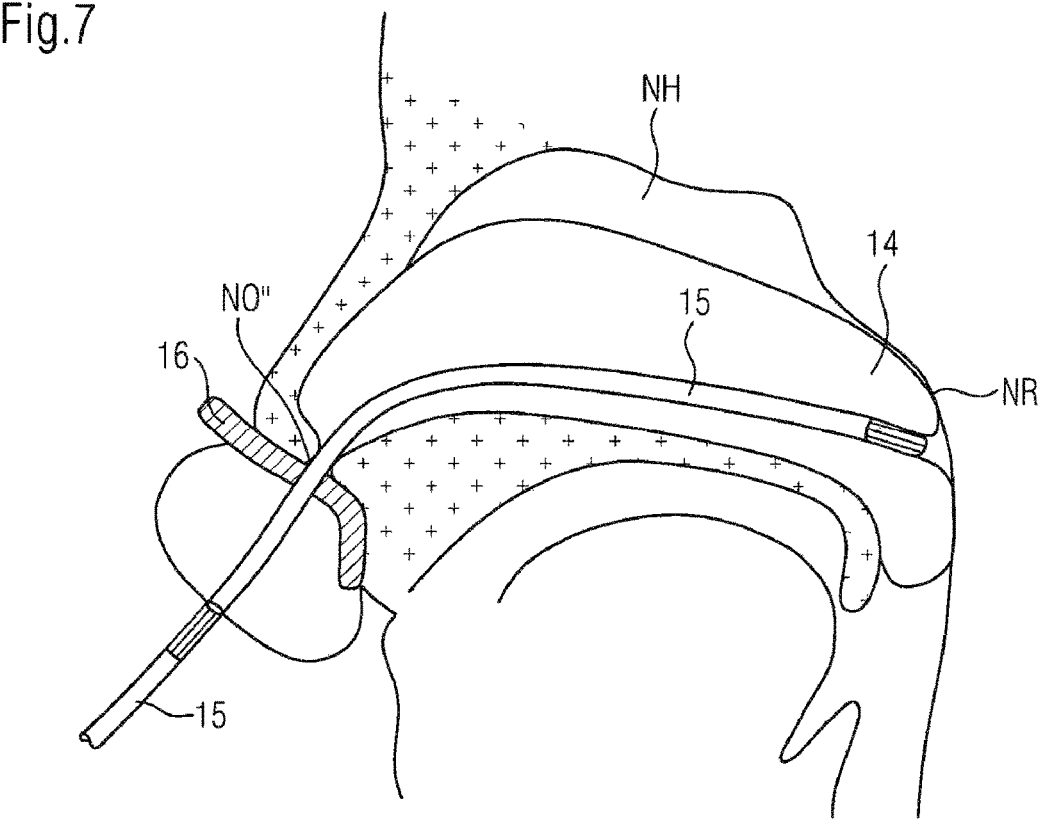
Figure 7A:
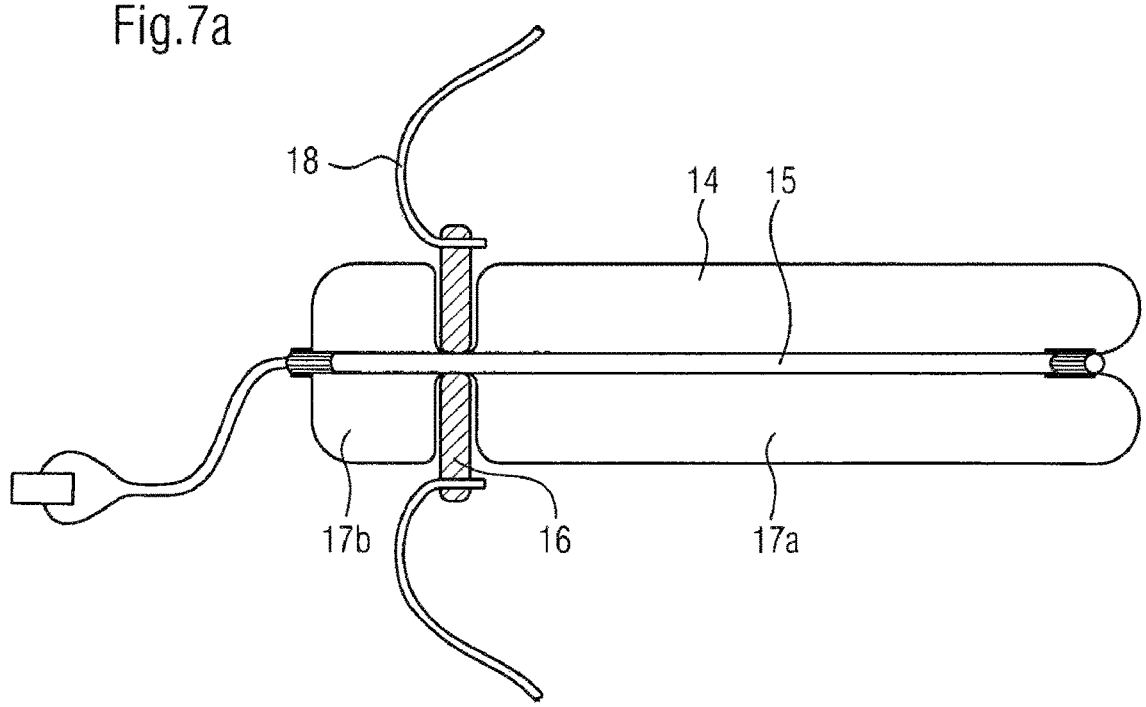

Further features, details, advantages and effects based on the invention are apparent from the following description of preferred embodiments of the invention and on the basis of the drawing, in which the functional and design principle of the tamponade according to the invention are explained in greater detail. The following is shown:

FIG. 1 an example of a freely unfolded tamponade body;

FIG. 2 an example of a tamponade body as in that has been inserted into a frontal sinus and charged with filling pressure;

FIG. 2*a* a cross-section tamponade body in the vicinity of the ostium;

FIG. 2*b* ion of the inserted tamponade in the vicinity the frontal sinus cavity;

FIG. 3 an embodiment of the tamponade with a residually elongated sinus cavity segment in situ, with the folded and compressed space-filling development of the balloon body that fills up the sinus cavities;

FIG. 4 an embodiment based on FIG. 1 with a front balloon body that is partially folded back;

FIG. 5 a sleeve element for spatially limiting the main nasal cavity segment of the balloon segment;

FIG. 5*a* a particular shortening and marking of the sleeve element;

FIG. 6 a fillable tamponade tube with a structure like a string of pearls;

FIG. 7 an embodiment of the blood tamponade for the complete tamponading of the main nasal cavity;

FIG. 7*a* the corresponding tamponade freely unfolded; and

Figure 8:
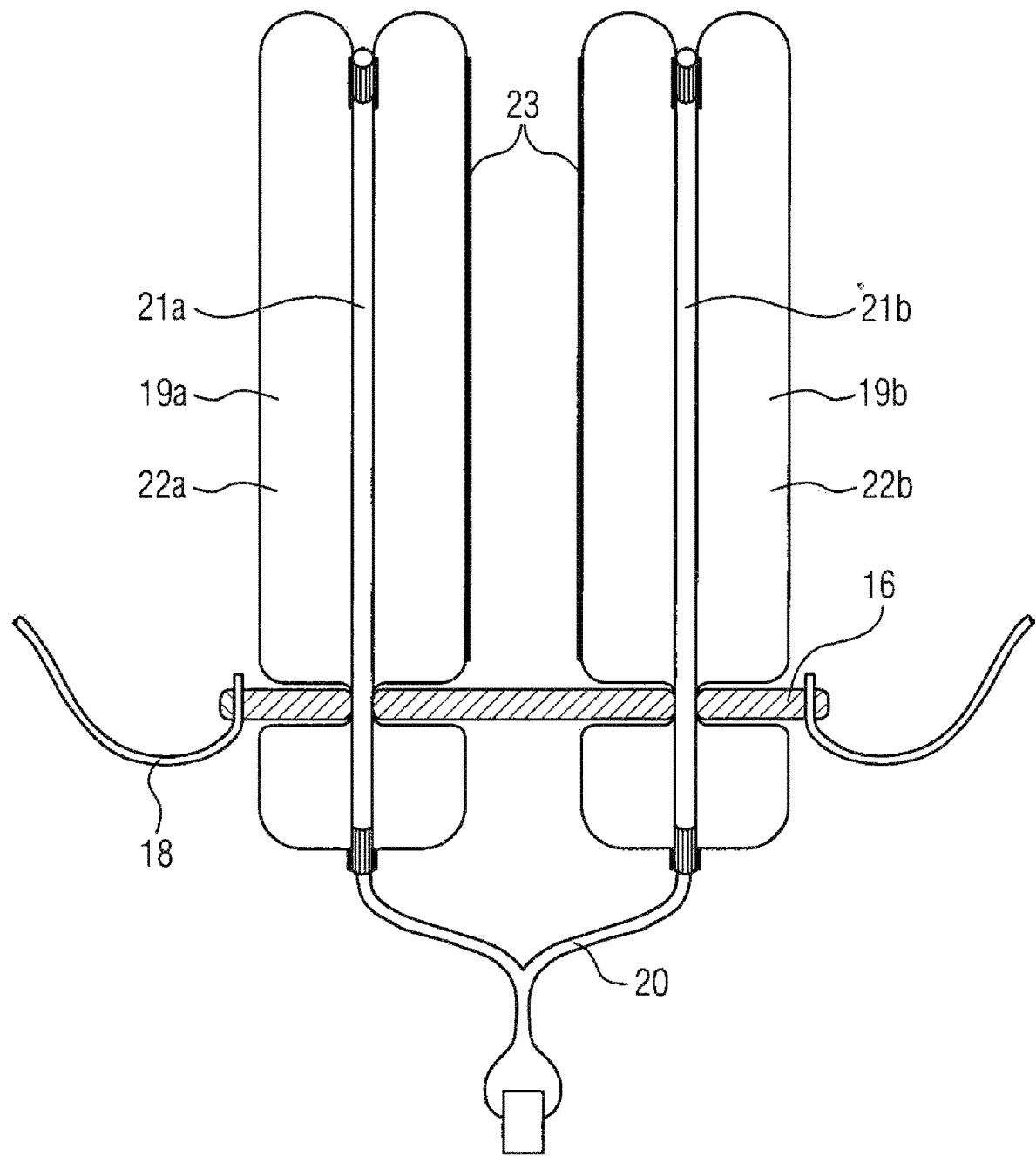

FIG. 8 a double-sided tamponade for the post-operative treatment correction the nasal septum.

DETAILED DESCRIPTION OF THE PREFERRED EMBODIMENTS

FIG. 1 represents a tamponade body 1 having a single-lumen shaft tube 2, on which a waisted balloon body 3 is supported. The balloon body is charged with a filling medium through a small-lumen filling line 4 at its proximal end. A pilot balloon 5 with an integrated one-way valve is disposed at the proximal end of the filling line.

The tamponade shown is structurally designed in particular for tamponading after the surgical widening of access passages to the frontal sinus. The distal portion 3*a* of the balloon, which is upstream of the balloon waist 7, is cylindrical and can have a diameter of ca. 30 mm with a length of ca. 50 mm. The proximal portion 3*b* of the balloon, which attaches rearwards to the waist, has a diameter of ca. 30 mm, for instance, with a length of ca. 20 to 30 mm. In the area of the constriction 7, the balloon tapers to a diameter of preferably 5 to 12 mm. The constriction or waist 7 is preferably configured with the smallest possible shoulder radii so that the shoulders of the waist are situated as vertical as possible when filled, which optimizes the anchoring effect of the waist in the ostium. The width of the constriction preferably measures ca. 3 to 8 mm, especially preferably 4 to 6 mm.

In the preferred embodiment, the balloon sheath itself consists of polyurethane (PUR) with Shore hardness of 80 A to 95 A or else 55 to 65 D. Elastollan materials produced by the BASF company or Pellethane by the Lubrizol company can be considered, for example. The wall thicknesses of the film lie in the range of cylindrical areas of balloon portions 3*a* and 3*b*, namely 5 to 50 μm, but preferably 5 to 15 μm. In the vicinity of the constriction, the thickness of the balloon walls should preferably be in the range from 1 to 40 μm. As an alternative to PUT, the balloon body 3 can also be made of PVC, LDPE, Pebax or comparable materials with sufficient mechanical strength and dimensional stability. Materials are preferred that remain dimensionally stable and inherently stable, particularly under tensile strain, in order to avoid undesirable slippage and to ensure tension-free anchoring of the tamponade in the ostium. Significantly compliant materials, such as silicone or latex, with low dimensional stability and the accompanying high tendency of the balloon body to slip are not preferred within the scope of the invention.

In the preferred embodiment, the shaft tube 2 is likewise manufactured of polyurethane. It should be as soft as possible and should ideally have the tension-free flexibility of cooked macaroni, but it should also hold open the tube lumen at a filling pressure of 30 to 60 mbar within the balloon. The shaft preferably consists of polyurethane with Shore hardness of 60 A to 90 A, especially preferably Shore hardness of 60 A to 70 A. In the event of a temporary radial collapse of the tube lumen, PUR-based shaft tubes usually straighten up elastically when the force diminishes. To avoid a permanent axial elastic straightening of the shaft tube that is typical of PUR, it can be provided with a rippled corrugation 8, in part or over its entire length, so that the shaft, which has an elastically axial orientation, can be bent smoothly. The rippled corrugation can additionally prevent a closure of the lumen due to the axial bending of the tube by up to 360 degrees.

The shaft tub 2 preferably has an outer diameter of 3 to 4 mm and an inner diameter of 1.5 to 2.5 mm. The distal end 2*a* of the shaft is preferably placed relative to the distal balloon shoulder such that, when fully unfolded, it does not project over the front radius of the balloon in the filled state.

FIG. 2 shows a tamponade body 1 placed in the access channel to the frontal sinus (ductus naso-frontalis). The tapered, constricted portion 7 of the balloon body is placed in the ostium SO of the frontal sinus. When the balloon is filled, the front portion 3*a* of the balloon body conforms to the walls of the frontal sinus. When filled, the rear proximal portion 3*b* of the balloon develops upstream of the ductus into the respectively adjacent space within the nasal cavity NH available for expansion. The space to unfold is defined by the upper nasal concha ON and the nasal septum.

Advantageous for the tamponading properties of the device is the sufficient residual dimensioning of the balloon diameter in the front portion 3*a*, which ensures that the balloon sheath conforms to the respective space while folding inward into the interior of the balloon, as a result of which the transmission of force onto the adjacent mucous membranes can be optimally uniform. Depending on the residual shaping of the balloon diameter, the forced transferred to the adjacent structures by the balloon can be approximately equated with the prevailing filling pressure within the balloon. For example, if filling pressures of ca. 20 mbar in the balloon are set barometrically by a suitable pump regulator, it can be assumed that the tamponading pressure exerted on the capillary vasculature is likewise ca. 20 mbar. Thus it is possible to set the transmural forces and maintain the capillary perfusion in a way that the user can measure and beyond the tamponading process. The particular way of folding the extremely thin-walled balloon sheath, which is residually dimensioned in the diameter, that is vital to regulating the effect of force on the tissue is schematically illustrated in FIGS. 2*a* and 2*b*.

FIG. 2*a* shows a section through the channel of the frontal sinus ostium. Owing to the residual configuration of the balloon waist 7, which is also preferred in this case, the segment conforms to any shape and dimension of the ostium that is to be assumed, without having to assume a tensioned state to tamponade on all sides. Particularly in the field of surgically widening the ostium or ductus, for instance, it is possible to adjust a perfusion-compatible tamponading effect that can be controlled and regulated extracorporeally.

FIG. 2*b* shows the advantageous folding of be described residual balloon sheath the vicinity of the frontal sinus SH. Prominent structures that protrude into the cavity are enclosed by the balloon sheath like a shell, without thereby forming pressure spikes by the elastic deformation of the balloon sheath. Instead, a largely homogeneous force effect by the tamponade is exerted on the exposed surfaces of the tamponade.

FIG. 3 shows an alternative form of a tamponade 1' with a residually elongated sinus cavity segment 3*a*, which expands in a bundle-like manner to into the frontal sinus to fill the space while spontaneously folding and bending along the longitudinal axis of the balloon body. For a tamponade of the frontal sinus such as this, the length of the front balloon cylinder 3*a* is increased to 5 to 10 cm, preferably 5 to 7 cm. In this configuration, the tube 2 supporting the front balloon segment has a particularly flexible but not elastically resilient bendability, and this permits it to follow the balloon body, which folds and bends in the cavity when filled, with as little tension as possible. The distal balloon segment 3*a* can have a concatenation of spherical, cylindrical or discoidal balloon segments, which are separated like a string of pearls. In this instance, the diameter of the separating constrictions is preferably at least 50% less than the diameter of the adjacent shaped segments. The diameters of the shaped segments, in turn, exceed the diameter of the ductus by at least 50% in the preferred embodiment.

In the tamponade 1" according to FIG. 4, the front end of the balloon portion 3*a* is partially folded back into the balloon body and is accommodated there by the free end of the tube 2. The junction between the balloon 3 and the tube preferably lies at least 10 mm above the balloon constriction 7. In this way, when less readily flexible materials are used for the support tube, an efficient space-filling tamponade can nevertheless be achieved, as described in FIG. 3, and any traumatizing effect of a shaft that is too rigid and has multiples bends over its course is avoided.

FIG. 5 shows an embodiment of the tamponade 1''', in which the balloon element 3*b* is elongated proximally to form a cylindrical segment. Its spatial expansion is limited by a slipped-on tube or sleeve element 8, which the surgeon slides over the segment 3*b* and is placed so as to achieve the desired trimming. In this embodiment, the axial length of the segment 3*b* can be increased to ca. 4 to 8 cm, preferably 4 to 6 cm. The option for adjustable unfolding the tamponade in the region upstream of the ostium can, on the one hand, optimize the quality of the anchoring of the tamponade in individual cases and, on the other hand, prevent the displacement of the nasal cavity and thus permit free nasal breathing.

FIG. 5*a* presents a special configuration of the sleeve element 8 and the shaft tube 2, which allows for particular advantages in the intra-operative placement of the tamponade by the surgeon. In this instance, the sleeve 8 is configured such that the emptied, unfilled tamponade body is entirely accommodated in the sleeve and can be displaced within the sleeve or relative to the sleeve with the least force possible, optimally such that it freely glides. The tamponade is enclosed in the sleeve such that the front distal end of the tamponade body is flush with the distal end 8*x* of the sleeve. During placement of the device, the distal end of the tamponade, which is enclosed in this way, can be gripped by the tips of the forceps and safely inserted into the transition from the main nasal cavity to the sinus cavity. The tamponade is then pushed forward relative to the sleeve that has been manually fixed in this position by the surgeon and into the sinus cavity. If a marking 2*a* applied to the shaft tube 2 reaches the proximal end 8*y* of the sleeve, the distal portion of the tamponade balloon 3*a* is pushed entirely out of the sleeve 8 and inserted into the sinus cavity. The tapered portion 7 of the tamponade body now lies flush with the distal end 8*x* of the sleeve. In this relative position of the sinus ostium, distal sleeve end 8*x* and taper 7, the distal balloon portion 3*a* is then charged with a first filling volume, whereby it unfolds into the sinus to fill the space. As the filling increases, the taper 7 is positioned in the anatomical transition area, anchors the device in this way and prevents the filled distal balloon body from sliding out. Following this, the sleeve 8 is drawn back relative to the SO in the fixed balloon so that the proximal balloon portion 3*b* can be released from the sleeve 8. The tamponade balloon is then filled to its final fill level. Finally, the sleeve is completely withdrawn from the nose; it is opened by tearing a longitudinal perforation 8*z* and is removed from the tamponade.

A tamponade tube according to the invention, which can be filled with a medium, is preferably inserted into a cavity of the viscerocranium that is bounded by an ostium when in the unfilled, evacuated or collapsed state in the manner of a gauze strip, effectively by packing it in with forceps. When the tamponade tube is filled through a proximally attached filling line, the tamponade develops into a bundle-like structure that fills the available space and is capable of filling up cavities, even those with complex shapes, in a tamponading manner with a uniform development of forces on its walls. The tamponade tube does not require a supporting shaft element. The inflatable packing tamponade can be evacuated after use and painlessly removed.

The tube body preferably consists of a micro-thin PUR with Shore hardness of 80 A to 90 A and has a wall thickness of 5 to 50 micrometers; or Shore hardness of 90 A and a wall thickness of 5 to 50 micrometers, preferably 10 to 12 micrometers.

The tube body can have a diameter of 4 to 20 mm, preferably a diameter of 4 to 12 mm, especially preferably a diameter of 5 to 8 mm.

The tube body can have a residual length that is 3 to 10 times the length of the cavity that is to be filled.

FIG. 6 shows a corresponding tamponade tube 11 with a waist area in the manner of a string of pearls. The segmented constrictions of spherical, cylindrical or discoidal segments 12 reduce the probability that portions of the tamponade bundles balled up within the cavity will slip out of the ostium leading to the cavity. In the resulting bundle, the waist areas 13 overlap and intersect with each other multiple times. The bundle is stabilized in this way. The diameter of the individual segments 12 in this case is preferably ca. 50% greater than the diameter of the ostium. The diameters of the waist areas 13 is preferably approximately half of the diameter of the ostium.

FIG. 7 shows a configuration of the tamponade as a blood tamponade 14 for the space-filling treatment of bleeding in the main nasal cavity NH. The longitudinal extension of the tamponade extends from the front nasal opening NÖ into the nasopharynx NR. When filled, it tightly seals the nasal cavity NH in this way and permits a stagnation pressure to set in on the bleed, which leads to the self-tamponading of oozing bleeds in areas of the nose that cannot be directly included in hemostatic compression. In particular, the invention allows for the patient to insert this type of invasive tamponade himself, which extends from the nasal opening to the rear wall of the nasopharynx. The invention proposes a substantially cylindrical balloon with a waist area in the distal region that is placed in the vicinity of the transition from the nasal cavity to the nasopharynx. The distal segment placed in the nasopharynx has a length of ca. 3 to 4 cm and has a diameter that is preferably smaller than that of the proximal intra-nasal balloon segment. The balloon body 17 rests upon a shaft tube 15 with an outer diameter of ca. 3.5 to 5 mm. The shaft has sufficient axial stability for the tamponade to be safely guided by the patient in the evacuated state without any further accessories and to be inserted into the lower nasal passage with only minimal irritation.

In its front region, the tamponade preferably comprises a freely displaceable discoidal element 16 with a continuous recess. Once the tamponade has been inserted, this disk-like element 16 can be slipped over the tamponade body 14 via its recess from the proximal to the distal end until it rests against the nasal opening. In this way, the displaceable disk 16 secures the position of the tamponade and fixes it at the desired insertion depth. The discoidal element 16 consists of a hard material and thus forms a hard structure in the region of the nasal ostium, on which the balloon of the tamponade body 14 tapers and is thereby anchored, in the vicinity of its transition between the distal segment (3*a*) of the balloon (3) and the proximal segment (3*b*) of the balloon (3), to the disk-like element 16 in the ostium.

During the subsequent filling, the distal balloon segment preferably unfolds first, which is achieved by supplying the filing medium to openings in the distal third of the tamponade. The proximal balloon segment that is delimited by the disk 16 is then successively filled by the overcurrent of medium, which discharges into it through the elastically tensioned, preferably narrow gap between the disk and the shaft. Thus a proximal segment is formed upstream of the disk and upstream of the nasal opening, and it contributes to stabilizing the position and insertion depth of the tamponade. The disk 16 can be provided with a retaining band 18, which is slung around the rear side of the ears like a nasal cannula for oxygen and fixed below the chin by a sleeve element.

FIG. 7*a* shows the tamponade 14 freely unfolded. The disk-like element 16 can be freely displaced onto the shaft tube under elastic tension. The element thereby limits the insertion depth and spatial expansion of the distal balloon 17*a* into the nasal cavity and into the nasopharyngeal area. The tamponade is preferably filled through a one-way valve via a short tube line.

In a modification of the embodiment described in FIG. 7, the present blood tamponades be of different lengths, extend only as far as the front, center or rear third of the nose. Tamponades are also possible which form tamponading segments only in individual sections of the nasal cavity, e.g. which do not reach the front one-third but are active in the center and rear third of the nose. The distal portions of the tamponading balloon can then have a diameter that is accordingly ineffective for tamponading.

Within the scope of the invention, FIG. shows two functionally coupled tamponade bodies 19*a*, 19*b*, which can be inserted to tamponade of the main nasal cavity following corrections performed on the nasal septum. The two branches 19*a* and 19*b* of the tamponade are connected at the front end by a Y-shaped structure 20, which straddles the bridge of the nose. The two balloon portions are filled at the same time via the inner lumen of the Y-shaped connector and are connected to each other such that they freely communicate.

In addition to using a shared filling tube 20, the two tamponade bodies 19*a*, 19*b* can also be coupled to each other by a common disk like element 16, which in this case has two recesses or ostia, each for the passage of one tamponade body 19*a*, 19*b*.

The free communication between the two balloon branches as well as the micro thin, residually dimensioned configuration of the balloon sheaths that are used adjust the surgically corrected nasal septum into a precise central position. Additionally, the two balloons 22*a*, 22*b* of the tamponade bodies 19*a*, 19*b* can include stabilizing, platelet-like rigid bodies 23 for supporting and splinting the fractured and still unstable bony septum on both sides.

All of the tamponades described in accordance with the invention can optionally be inserted using a guiding stylet, which is removed from the tamponade once it is placed.

The tamponade bodies are filled preferably with air as the medium.

A particular advantage in the use of the technology according to the invention is also the possible optical transparency of the balloon material in the described embodiment made of micro-thin polyurethane, since it allows the surgeon to see through the balloon sheath largely without being visually obstructed and to directly inspect the state of the wound and tissue surrounding the tamponade. If the tamponade pressure is too high, a pale coloration of the tissue can be seen and recognized in this way, for instance. By reducing the filling pressure in the tamponade, when air is used as the medium, the surgeon can then establish rosy tissue that is well supplied with blood, which positively supports the progress of the wound healing.

A further and more important aspect is that the outer side of the balloon is as smooth as possible in a tamponade body according to the invention. An average residual roughness should be less than 5 μm, e.g. less then 2 μm, preferably less than 1 μm, especially less than 0.5 μm.

The tamponade body according to the invention is designed for cavities in the region of the nasal tract, wherein the space to be filled naturally has a particular rigidity to its walls as well as an inner spatial complexity. Based on the principle of residual dimensioning described above, these spaces can be tamponaded in a manner compatible with perfusion with a low level of planar homogeneous compressive force.

The invention claimed is:

1. A tamponade for nasal cavities or sinus cavities (1; 1'; 1"; 1'''; 11; 14; 19*a*, 19*b*) for tamponading a cavity of the nasal tract in the region of an ostium leading to the cavity with uniform force, comprising a thin-walled balloon (3), which is made from a smoothly folding polyurethane material, with a wall thickness in the range of 5 to 50 μm, which is already completely shaped with the required tamponade dimensions or greater at the time of production, and can therefore be expanded without application of filling pressure, and said balloon is configured to be placed relative to the cavity to be tamponaded in such a way that it occupies the respective, generally irregular-shaped cavity and the ostium of same when in a filled condition, through the development of uniform forces on the structures exposed to the balloon (3) in such a way that a distal segment (3*a*) of the balloon (3) is located inside the cavity where a tamponade is to be applied, a proximal segment (3*b*) of the balloon (3) is located upstream of the cavity and a transostial segment of the balloon (3) extends through the ostium and connects the distal segment (3*a*, 3*b*) of the balloon (3) to the proximal segment (3*b*) of the balloon (3), wherein the transostial segment of the balloon (3) is tapered relative to the proximal and distal segments (3*a*, 3*b*) of the balloon (3) in the deployed state of the balloon, and the tamponade for nasal cavities or sinus cavities (1; 1'; 1"; 1'''; 11; 14; 19*a*, 19*b*) is anchored in the transition region and secured in position, wherein each of the distal segment (3*a*), the proximal segment (3*b*) and the tapered transostial segment is penetrated by a continuous tube (2), and the distal segment (3*a*) and the proximal segment (3*b*) are fixed to the tube (2).

2. The tamponade for nasal cavities or sinus cavities (1; 1'; 1"; 1'''; 11; 14; 19*a*, 19*b*) according to claim 1, characterized in that the balloon (3) is configured to be placed relative to the cavity to be tamponaded in such a way that it rests on the surface of the cavity and/or the ostium so as to form multiple, largely untensioned folds in a balloon sheath.

3. The tamponade for nasal cavities or sinus cavities (1; 1'; 1"; 1'''; 11; 14; 19*a*, 19*b*) according to claim 1, characterized in that the balloon (3) is configured to be placed relative to the cavity to be tamponaded in such a way that it rests on the surface of the cavity while largely avoiding the remaining residual spaces.

4. The tamponade for nasal cavities or sinus cavities (1; 1'; 1"; 1'''; 11; 14; 19*a*, 19*b*) according to claim 1, characterized in that a sheath of the balloon (3) is untensioned in the region of the ostium and rests on a non-stretchable structure that is arranged there without tension-related pressure, and so the surface pressure exerted on the surface of the ostium corresponds to the surface pressure exerted on the surface of the cavity.

5. The tamponade for nasal cavities or sinus cavities (1; 1'; 1"; 1'''; 11; 14; 19*a*, 19*b*) according to claim 1, characterized in that the polyurethane material of the balloon (3) falls within the Shore durometer range of 80 Å to 95 Å.

6. The tamponade for nasal cavities or sinus cavities (1; 1'; 1"; 1'''; 11; 14; 19*a*, 19*b*) according to claim 1, characterized in that the balloon (3) has a wall thickness of 5 to 25 μm, in the vicinity of its largest diameter.

7. The tamponade for nasal cavities or sinus cavities (1; 1'; 1"; 1'''; 11; 14; 19*a*, 19*b*) according to claim 1, characterized in that the balloon (3) has a wall thickness of 10 to 20 μm, in the vicinity of its largest diameter.

8. The tamponade for nasal cavities or sinus cavities (1; 1'; 1"; 1'''; 11; 14; 19*a*, 19*b*) according to claim 1, characterized in that the balloon (3) consists of an optically transparent material, which permits the visual inspection of the tissue adjacent to the nasal cavity or sinus cavity tamponade (1; 14; 19*a*; 19*b*).

9. The tamponade for nasal cavities or sinus cavities (1; 1'; 1"; 1'''; 11; 14; 19*a*, 19*b*) according to claim 1, characterized in that the balloon (3) is configured to be placed relative to the cavity to be tamponaded in such a way that, in the transition region from the distal balloon segment (3*a*) lying within the cavity to be tamponaded to the region of the proximal balloon segment (3*b*) lying upstream of the cavity, the balloon (3) is provided with a taper (7, 13) or constriction, which anchors the tamponade (1; 14; 19*a*; 19*b*) in the transition region to the ostium and secures it in its position.

10. The tamponade for nasal cavities or sinus cavities (1; 1'; 1"; 1'''; 11; 14; 19*a*, 19*b*) according to claim 9, characterized in that the diameter of the taper (7, 13) or constriction is at least 50% smaller than the diameter of the distally adjacent balloon segment.

11. The tamponade for nasal cavities or sinus cavities (1; 1'; 1"; 1'''; 11; 14; 19*a*, 19*b*) according to claim 1, characterized in that the distal segment (3*a*) of the balloon (3) is residually elongated such that it develops into the form of a folded and/or coiled, space-filling bundle when placed in the cavity to be filled and then inflated.

12. The tamponade for nasal cavities or sinus cavities (1; 1'; 1"; 1'''; 11; 14; 19*a*, 19*b*) according to claim 1, characterized in that the distal segment (3*a*) of the balloon (3) is two to ten times as long, or is two to five times as long, as the cavity to be tamponaded.

13. The tamponade for nasal cavities or sinus cavities (1; 1'; 1"; 1'''; 11; 14; 19*a*, 19*b*) according to claim 1, characterized in that the balloon (3) does not have an opening at its distal end or in that an opening there is close-sutured.

14. The tamponade for nasal cavities or sinus cavities (1; 1'; 1"; 1'''; 11; 14; 19a, 19b) according to claim 1, characterized in that the support tube (2) does not have an opening at its distal end or in that an opening there is close-sutured.

15. The tamponade for nasal cavities or sinus cavities (1; 1'; 1"; 1'''; 11; 14; 19a, 19b) according to claim 14, characterized in that only the proximal end of the balloon (3) is applied to the support tube (2).

16. The tamponade for nasal cavities or sinus cavities (1; 1'; 1"; 1'''; 11; 14; 19a, 19b) according to claim 15, characterized in that the support tube (2) or a filling tube extends into the distal segment (3a) of the balloon (3) that fills the sinus cavity and is sealingly connected there at its distal end to the distal end of the balloon (3).

17. The tamponade for nasal cavities or sinus cavities (1; 1'; 1"; 1'''; 11; 14; 19a, 19b) according to claim 1, characterized in that the support tube (2) is configured such that it is elastically deformable and/or has a wall thickness of 0.1 to 0.3 mm.

18. The tamponade for nasal cavities or sinus cavities (1; 1'; 1"; 1'''; 11; 14; 19a, 19b) according to claim 1, characterized in that the support tube (2) is molded with a rippled corrugation to improve its straightening properties.

19. The tamponade for nasal cavities or sinus cavities (1; 1'; 1"; 1'''; 11; 14; 19a, 19b) according to claim 1, characterized in that the configuration of the proximal segment (3b) of the balloon (3) and its longitudinal extent can be limited by a sleeve element (8), which is pushed over the support tube (2) and the collapsed balloon (3).

20. The tamponade for nasal cavities or sinus cavities (1; 1'; 1"; 1'''; 11; 14; 19a, 19b) according to claim 1, characterized in that it comprises a freely displaceable disk-like element (16) of a hard material with a continuous recess, which can be slipped over the balloon (3) and thus forms a hard structure in the region of a nasal ostium, on which the balloon (3) tapers and is thereby anchored, in the vicinity of its transition between the distal segment (3a) of the balloon (3) and the proximal segment (3b) of the balloon (3), in the region of a nasal ostium.

21. A tamponade (1; 1'; 1"; 1'''; 11; 14; 19a, 19b) for a simultaneous tamponade of nasal cavities or sinus cavities in the left and right halves of the viscerocranium, each in the region of an ostium leading to the cavity with uniform force, comprising two thin-walled balloons (22a, 22b), which are made from a smoothly folding polyurethane material, with a wall thickness in the range of 5 to 50 μm, which is already completely shaped with the required tamponade dimensions or greater at the time of production, and can therefore be expanded without application of filling pressure, and said balloons (22a, 22b) are configured to be placed relative to the cavities to be tamponaded in such a way that each of said balloons (22a, 22b) occupies the respective, generally irregular-shaped cavity and the ostium of same when in a filled condition, through the development of uniform forces on the structures exposed to the balloon (22a, 22b) in such a way that a distal segment (3a) of each balloon (22a, 22b) is located inside the cavity where a tamponade is to be applied, a proximal segment (3b) of each balloon (22a, 22b) is located upstream of the cavity and a transostial segment of each balloon (22a, 22b) extends through the ostium and connects the distal segment (3a, 3b) of the balloon (22a, 22b) to the proximal segment (3b) of the balloon (22a, 22b), wherein the transostial segment of each balloon (22a, 22b) is tapered relative to the proximal and distal segments (3a, 3b) of the balloon (22a, 22b) in the deployed state of the balloon (22a,22b), and the tamponade for nasal cavities or sinus cavities (1; 1'; 1"; 1'''; 11; 14; 19a, 19b) is anchored in the transition region and secured in position, wherein each of the distal segment (3a), the proximal segment (3b) and the tapered transostial segment of each balloon (22a, 22b) is penetrated by a continuous tube (21a, 21b), and wherein a free connection is established between the two balloons (22a, 22b), such as by means of a common fixation plate (16), which is configured to fix the intermediate anatomical structures in position while applying a homogenous force to both sides.

22. The tamponade for nasal cavities or sinus cavities (1; 1'; 1"; 1'''; 11; 14; 19a, 19b) according to claim 21, characterized in that one or both of the two balloons (22a, 22b) that are provided for simultaneously tamponading cavities in the left and right halves of the viscerocranium support a splint (23), or one splint each, consisting of a solid material, wherein two splints (23) of this type are arranged facing each other.

* * * * *